US012551725B2

(12) United States Patent
Winfield et al.

(10) Patent No.: US 12,551,725 B2
(45) Date of Patent: Feb. 17, 2026

(54) PATIENT POSITIONING FOR RADIOTHERAPY TREATMENT

(71) Applicant: Elekta Limited, Crawley (GB)

(72) Inventors: Colin Winfield, Crawley (GB); Johan Tegin, Crawley (GB); Ana Folgueras, Cawley (GB)

(73) Assignee: Elekta Limited, Crawley (GB)

( * ) Notice: Subject to any disclaimer, the term of this patent is extended or adjusted under 35 U.S.C. 154(b) by 643 days.

(21) Appl. No.: 17/997,712

(22) PCT Filed: Apr. 29, 2021

(86) PCT No.: PCT/EP2021/061352

§ 371 (c)(1),
(2) Date: Nov. 1, 2022

(87) PCT Pub. No.: WO2021/219831

PCT Pub. Date: Nov. 4, 2021

(65) Prior Publication Data

US 2023/0226377 A1 Jul. 20, 2023

(30) Foreign Application Priority Data

May 1, 2020 (GB) ..................................... 2006472

(51) Int. Cl.
*A61N 5/10* (2006.01)

(52) U.S. Cl.
CPC ........... *A61N 5/107* (2013.01); *A61N 5/1049* (2013.01); *A61N 2005/1095* (2013.01)

(58) Field of Classification Search
CPC .................. A61N 5/107; A61N 5/1049; A61N 2005/1095; A61N 2005/1054; A61N 5/1064; A61N 5/1075; A61N 2005/1061
See application file for complete search history.

(56) References Cited

U.S. PATENT DOCUMENTS 5,099,505 A * 3/1992 Seppi ..................... A61B 6/583
378/65
5,168,532 A * 12/1992 Seppi ..................... H04N 23/30
348/217.1

(Continued)

FOREIGN PATENT DOCUMENTS

EP 2664360 A2 11/2013
GB 2522914 A 8/2015

(Continued)

OTHER PUBLICATIONS

"International Application Serial No. PCT/EP2021/061352, International Search Report dated Aug. 10, 2021", (Aug. 10, 2021), 6 pgs.

(Continued)

*Primary Examiner* — David A Vanore

(74) *Attorney, Agent, or Firm* — Schwegman Lundberg & Woessner, P.A.

(57) ABSTRACT

Disclosed herein is a method of positioning a patient for radio-therapy treatment using a radiotherapy device. The method comprises determining an identity of a treatment beam that is to be used to treat the patient, determining an offset between a reference location and an isocentre location for the identified treatment beam that is to be used to treat the patient, and changing a spatial relationship between the patient and at least a part of the radiotherapy device, according to the determined offset.

19 Claims, 5 Drawing Sheets

(56) References Cited

U.S. PATENT DOCUMENTS

Figure 1:
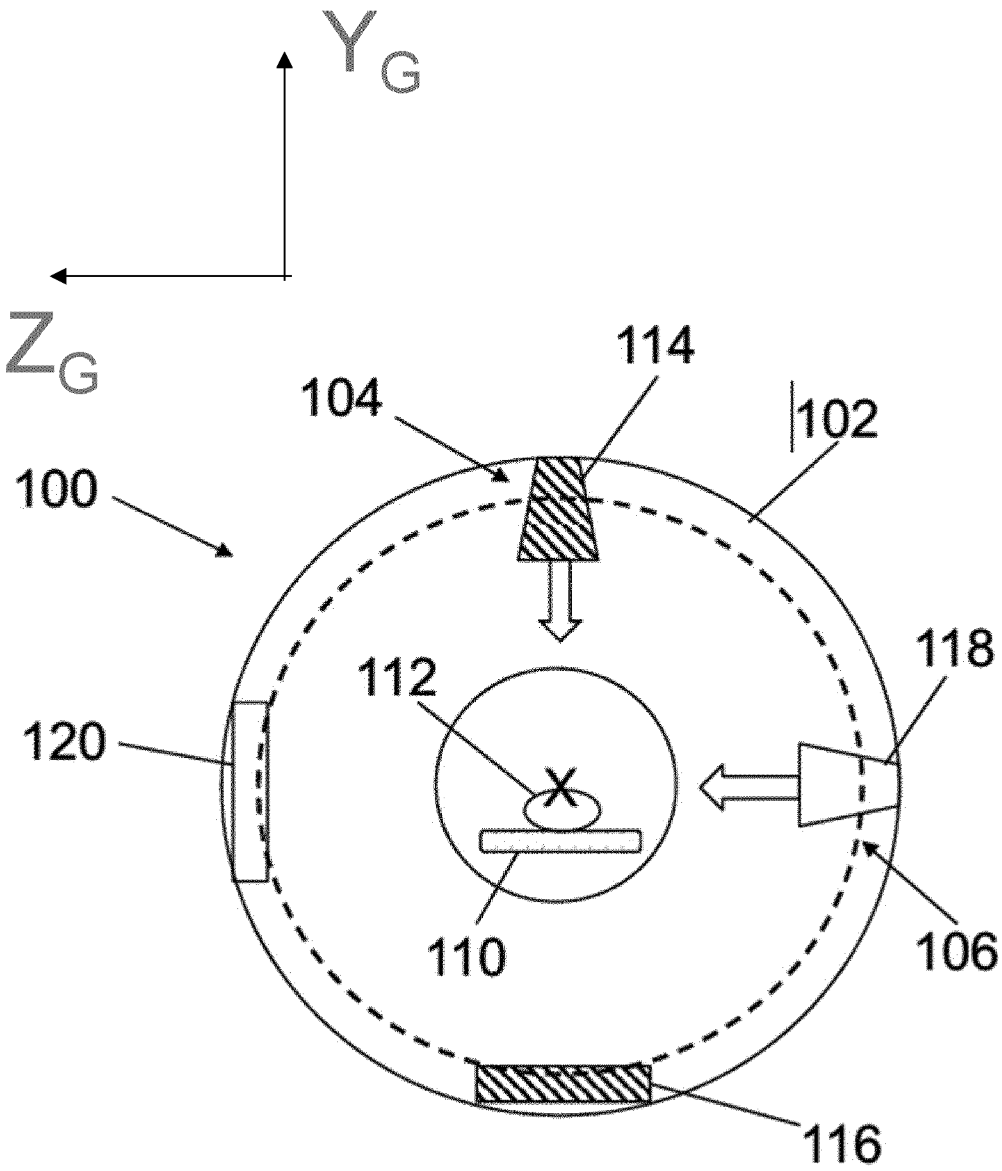

| | | | | | |
|---|---|---|---|---|---|
| 5,825,845 | A * | 10/1998 | Blair | A61N 5/1049 | 378/65 |
| 6,490,335 | B1 * | 12/2002 | Wang | A61B 6/027 | 378/4 |
| 8,170,319 | B2 * | 5/2012 | Shukla | A61N 5/1049 | 378/65 |
| 11,627,920 | B2 * | 4/2023 | Mazin | A61N 5/1067 | 250/363.04 |
| 11,633,626 | B2 * | 4/2023 | Voronenko | A61N 5/1031 | 378/65 |
| 11,712,584 | B1 * | 8/2023 | Dooley | A61N 5/1067 | 378/65 |
| 11,712,586 | B2 * | 8/2023 | Cox | A61N 5/1045 | 378/65 |
| 11,801,398 | B2 * | 10/2023 | Voronenko | A61N 5/103 | |
| 11,813,481 | B2 * | 11/2023 | Pal | A61N 5/1065 | |
| 11,904,184 | B2 * | 2/2024 | Maolinbay | A61N 5/1049 | |
| 2005/0059887 | A1 * | 3/2005 | Mostafavi | A61B 6/4417 | 600/431 |
| 2005/0109939 | A1 * | 5/2005 | Engler | G01J 1/00 | 378/65 |
| 2006/0017022 | A1 * | 1/2006 | Rigney | B25J 9/1666 | 250/497.1 |
| 2009/0003528 | A1 * | 1/2009 | Ramraj | A61B 6/08 | 378/119 |
| 2009/0168961 | A1 * | 7/2009 | Hieronimi | A61N 5/1049 | 378/65 |
| 2010/0155621 | A1 * | 6/2010 | Balakin | H05H 13/04 | 315/503 |
| 2011/0211665 | A1 * | 9/2011 | Maurer, Jr. | A61N 5/1039 | 378/19 |
| 2013/0315367 | A1 * | 11/2013 | Knox | A61B 6/466 | 378/19 |
| 2014/0171726 | A1 * | 6/2014 | Gum | A61B 6/032 | 600/1 |
| 2016/0023019 | A1 * | 1/2016 | Filiberti | A61N 5/1075 | 600/1 |
| 2016/0074673 | A1 * | 3/2016 | Allen | A61N 5/1049 | 600/1 |
| 2017/0128750 | A1 * | 5/2017 | Filiberti | A61N 5/1069 | |
| 2017/0203125 | A1 * | 7/2017 | Amato | A61N 5/1039 | |
| 2018/0056091 | A1 * | 3/2018 | Jordan | A61N 5/107 | |
| 2018/0071551 | A1 * | 3/2018 | Berlinger | G06T 7/0012 | |
| 2019/0076672 | A1 * | 3/2019 | Nord | A61N 5/1048 | |
| 2019/0184197 | A1 * | 6/2019 | Fallone | A61N 5/1071 | |
| 2020/0171328 | A1 * | 6/2020 | Shea | A61B 6/0487 | |
| 2022/0395243 | A1 * | 12/2022 | La Riviere | A61B 6/032 | |
| 2023/0211182 | A1 * | 7/2023 | Winfield | A61N 5/1049 | 378/65 |
| 2023/0248999 | A1 * | 8/2023 | Eriksson | A61B 6/4266 | 378/65 |
| 2023/0263489 | A1 * | 8/2023 | Carlsson | A61N 5/1077 | 378/4 |

FOREIGN PATENT DOCUMENTS

| | | | | | |
|---|---|---|---|---|---|
| GB | 2537120 | A | 10/2016 | | |
| WO | WO-2019050551 | A1 | 3/2019 | | |
| WO | WO-2019063035 | A2 * | 4/2019 | A61N 5/1075 | |

OTHER PUBLICATIONS

"International Application Serial No. PCT/EP2021/061352, Written Opinion dated Aug. 10, 2021", (Aug. 10, 2021), 8 pgs.

"United Kingdom Application Serial No. 2006472.1, Combined Search and Examination Report mailed Oct. 28, 2020", (Oct. 28, 2020), 5 pgs.

"European Application No. 21 723 690.0, Office Action dated Oct. 8, 2025", Oct. 8, 2025, 7 pgs.

* cited by examiner

PATIENT POSITIONING FOR RADIOTHERAPY TREATMENT

PRIORITY APPLICATIONS

This application is a U.S. National Stage Filing under 35 U.S.C. § 371 from International Application No. PCT/EP2021/061352, filed on Apr. 29, 2021, and published as WO2021/219831 on Nov. 4, 2021, which claims the benefit of priority to United Kingdom Application No. 2006472.1, filed on May 1, 2020; the benefit of priority of each of which is hereby claimed herein, and which applications and publication are hereby incorporated herein by reference in their entireties.

FIELD

This disclosure relates to methods of positioning a patient for radiotherapy treatment using a radiotherapy device. In particular it relates to methods of positioning a patient for radiotherapy treatment using a radiotherapy device that can deliver multiple different treatment beams. This disclosure further relates to determination of a patient position for improved radiotherapy treatment.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour.

A radiotherapy device typically comprises a gantry which supports a treatment apparatus that comprises a beam generation system, or other source of radiation, which is rotatable around a patient. For example, for a linear accelerator (linac) device, the beam generation system may comprise a source of radio frequency energy, a source of electrons, an accelerating waveguide, and beam shaping apparatus.

For the purposes of radiotherapy treatment, it is desirable to deliver a particular dose to a target region, as prescribed by a treatment plan, while minimising the dose to surrounding areas of healthy tissue. Radiotherapy systems typically deliver beams of MegaVolt (MV) radiation energy from different angles to the area to be treated, i.e. the target region. In this way, each portion of healthy tissue surrounding the target region is only exposed to the radiation beam intermittently, at particular angles, whilst the target region is exposed to the MV radiation beam throughout treatment, at every angle.

Some radiotherapy devices, such as devices capable of performing Image Guided Radiotherapy (IGRT), include imaging capabilities. The images of a patient that are provided by an imaging apparatus may be used to assist with treatment planning and positioning of the patient. The imaging apparatus may for example comprise a source of kilovolt (kV) energy radiation, such as X-rays. The imaging apparatus is typically mounted on the rotatable gantry of the radiotherapy device, spatially separated from the treatment apparatus.

It is common practice for initial images, or reference images, to be obtained of a patient in order for a health professional to provide a radiotherapy treatment plan specific to that patient. The reference images are typically obtained using an imaging device other than the imaging apparatus of a radiotherapy device. For example, they may be obtained using a computed tomography (CT) scanner. The reference images may be obtained relatively far in advance of the radiotherapy treatment occurring, for example a few weeks beforehand. It is also common practice for up-to-date, pre-treatment images to be obtained, immediately (or at least very shortly) before radiotherapy treatment commences. For example, pre-treatment images may be obtained using the imaging apparatus of an IGRT device. The imaging apparatus may be mounted on a rotatable gantry. The gantry may also have treatment apparatus (for generating one or more radiotherapy beams) mounted thereon. Before radiotherapy treatment commences, an alignment process should be carried out, to align the patient's position in the pre-treatment images to his or her position in the reference images. This process may be referred to as 'registration'. For example, particular aspects of the patient's anatomy may be used as landmarks and any change in position of those landmarks, between the two sets of images, may be observed. The patient can then be positioned or repositioned, in accordance with those observations.

A radiotherapy device with a rotatable source of radiation has a treatment isocentre (or beam isocentre), which for an MV radiation source may be referred to as an MV isocentre. Knowledge of the position (or location) of the MV isocentre, and its position with respect to a target region within a patient, is important for accurate positioning of the patient for radiotherapy treatment. In a mechanically ideal system, the isocentre can be thought of as the point in space that is intersected by the treatment beam at all angles of gantry rotation. However, due to real-world effects, and in particular due to the mechanical flexing of components which connect the heavy treatment head of the linac to the gantry as a function of gantry rotation angle, it is typical to model the isocentre as a small virtual volume.

In order for images to be used for guiding radiotherapy treatment, and for accurately positioning the patient on the day of treatment, the position of the beam isocentre in those image(s) should be accurately known. It is known to perform a calibration by mapping the position of the beam isocentre in images taken by the imaging apparatus as a function of gantry angle, and correcting for the effects of the above-mentioned small flexes during gantry rotation using a reconstruction algorithm. This calibration is, according to known methods, performed for one treatment beam, at a particular energy and having particular characteristics. However, the position of the isocentre for a radiotherapy device may change, for example when a treatment beam is recalibrated, and/or when a treatment beam of a different energy is used, and/or when a filter is added or changed or removed from a beam at a particular energy and/or when the angle of delivery of the beam changes, for example when the beam switches from a coplanar to a non-coplanar configuration. If this difference in isocentre position is not accounted for, the accuracy of any subsequent radiotherapy treatment may be sub-optimal. Any deviation between the isocentre positions before and after beam recalibration, or while swapping between beam energies or between other beam characteristics in a multi-beam device, are likely to be extremely small, and certainly such deviations fall within currently acceptable quality assurance (QA) guidelines and clinical tolerances. However, improvements in the accuracy of isocentre measurements above and beyond even these high standards are desirable to ensure patients receive the highest standard of treatment.

It has been speculated that it may be possible to address any minor misalignment between isocentres of multiple energies via an intensive QA procedure which involves bringing the isocentres of the beams of every available energy into alignment by adjusting the radiation beam steering parameters associated with each treatment beam energy. However, bringing the isocentres of each treatment beam into alignment with one another in this way would be extremely labour-intensive, and significantly increase the length of acceptance testing, commissioning, and subsequent QA routines for a radiotherapy device. Such a method would have to be re-run after any of the beams was recalibrated or adjusted, which would be time consuming and would reduce the availability of the radiotherapy device for clinical use. Moreover, such a time consuming and labour intensive process poses a risk that some users may not carry it out as thoroughly or as often as would be required to achieve optimal results.

The present application seeks to address these and other disadvantages encountered in the prior art.

SUMMARY

An improved method, apparatus, system and controller are provided which enable a correction or alignment to be made in order to account for a difference in beam isocentre position (or location) for different respective beams, for radiotherapy treatment by a radiotherapy device.

The improved method comprises determining an offset between a reference position or location and a position or location of an isocentre of a treatment beam that can be provided by a radiotherapy device. For example, the offset may comprise an 'isocentre offset' between a position or location of a reference isocentre, which is an isocentre of a first 'reference' treatment beam that can be provided by the radiotherapy device, and a position or location of an isocentre of a second, different treatment beam, which can also be provided by the radiotherapy device, and which is actually intended for use in providing radiotherapy treatment to a particular patient. The method may comprise moving the patient according to that determined offset, for example the determined isocentre offset. The first and second treatment beams may comprise beams of first and second respectively different identities. A beam's identity may comprise one or more of its characteristics, such as its energy, angle of delivery, and whether it comprises a filter, such as a flattening filter, or whether it is a 'flattening filter free' (fff) beam. By way of non-limiting example, the first treatment beam may be a 6 MV beam and the second treatment beam may be a 10 MV beam, or vice versa.

The position or location of the reference isocentre (i.e. the isocentre of a 'reference' radiotherapy treatment beam) may be used, to make an initial alignment of a patient (or of an image such as a pre-treatment image of the patient) to the treatment apparatus of a radiotherapy device, in accordance with a pre-defined treatment plan. That alignment may then be made more accurate, by incorporating the determined isocentre offset, between the reference beam and the intended treatment beam, therein.

It is known to register pre-treatment images, which are obtained using the image capture apparatus of a radiotherapy device, usually immediately before treatment is to commence, against reference images that were taken previously, and which have formed the basis of the treatment plan that has been created for the patient. Usually, that registration will take place on a calibrated system, which already takes into account a spatial relationship between the image centre of a pre-treatment image (or another point in the pre-treatment image) and a beam isocentre for the treatment apparatus of the radiotherapy device. For example, that calibration may involve compiling the pre-treatment image as a three-dimensional image, from a plurality of two-dimensional images, wherein the manner in which the two-dimensional images are combined with one another provide a calibration of the resultant three-dimensional pre-treatment image to the treatment apparatus of the radiotherapy device. But conventionally that calibration been done using the beam isocentre for a single 'reference' beam only, which the treatment apparatus can output. The reference beam will be of a particular energy and/or of a particular angle of delivery, and will have other particular identifying characteristics, such as being a filtered or filter-free beam, and having a certain beam profile. The improved methods disclosed herein incorporate an additional offset to account for the fact that, if a different beam (other than the reference beam) is to be used to treat a patient, which has one or more characteristics that differ from the characteristics of the reference beam, the precise location of the treatment beam isocentre, as will be actually applied to the patient during subsequent radiotherapy treatment, may be different to the reference beam isocentre that has been used for the image registration and/or calibration.

If a treatment beam (that can be output by the treatment apparatus of a radiotherapy device) is recalibrated, or undergoes any other changes, for a single beam identity, the beam's isocentre position/location can be checked and, if necessary, updated for that beam identity, and updated offsets can be applied for subsequent radiotherapy treatments accordingly, without disturbing the beam isocentre positions for other beam identities and without the need to change any calibration maps or other aspects of the radiotherapy system or to regenerate existing treatment plans to accommodate the change in the relative isocentre offset. When the location of the isocentre for a beam changes, the radiotherapy system may be updated to store (or have access to) the updated spatial relationships between that isocentre and one or more isocentres of respective other beams, which can be generated by the radiotherapy device.

A radiotherapy device, or a radiotherapy system, or an associated controller, may be configured to demand a check or a redetermination of one or more beam isocentre positions at certain times—for example, when the beam parameters for a beam of a particular identity are adjusted during a quality assurance (QA) or calibration procedure, and/or after a particular length of time or number of treatments, and so on.

According to an aspect, a method is provided of positioning a patient for radiotherapy treatment using a radiotherapy device. The method comprises determining an identity of a treatment beam that is to be used to treat the patient, determining an offset between a reference location and an isocentre location for the identified treatment beam that is to be used to treat the patient, and changing a spatial relationship between the patient and at least a part of the radiotherapy device, according to the determined offset.

The radiotherapy device may be configured to move between at least a first and a second configuration, each configuration being associated with a respective treatment beam identity, and determining the identity of the treatment beam to be used to treat the patient can comprise determining whether the device is in, or will be in, the first or second configuration.

The first configuration may be a coplanar configuration, and the second configuration may be a non-coplanar configuration.

The radiotherapy device can be configured to deliver treatment beams from each of a plurality of angles with respect to a patient longitudinal axis, and determining the identity of the treatment beam to be used to treat the patient can comprise determining which angle of the plurality of angles the treatment beam will be delivered from.

The identity of the treatment beam that is to be used to treat the patient may comprise one or more characteristics of the treatment beam that is to be used to treat the patient. The one or more characteristics may comprise any of: an angle at which the treatment beam is or would be delivered, an energy at which the treatment beam is or would be delivered; a beam profile; the presence or absence of a filter on the treatment beam; and, if a filter is present, what type of filter it is.

The reference location may comprise a focal point of an image of the patient. For example, it may comprise the focal point of a reference image that was used to help create a patient-specific treatment plan, for the patient.

The reference location may comprise any suitable location that has been predetermined, relative to the treatment apparatus (or to another aspect) of the radiotherapy device. Each of the treatment beams that can be output by the treatment apparatus will have a respective isocentre, wherein the relative locations of those isocentres may have been predetermined, relative to the reference location.

The reference location may comprise a location of an isocentre of a treatment beam of an identity that is different to the identity of the treatment beam that is to be used to treat the patient. The reference location may comprise a location of an isocentre of a reference beam, which can be output by the radiotherapy device. The reference location may comprise an isocentre of a calibrated treatment beam.

The reference location may be an assumed location of the intended treatment beam's isocentre, wherein that assumed location has been previously used during the acquisition, calibration, or alignment of one or more images, which the subsequent radiotherapy will rely on and/or be based upon.

The reference location and/or the isocentre location for the identified treatment beam that is to be used to treat the patient may be defined within, or in relation to, an image of at least part of the patient, for example a pre-treatment image and/or a reference image. The image, or one or more landmarks within the image, may be aligned or calibrated with respect to the reference location. The landmarks may comprise one or more target regions or sub-regions, towards which radiotherapy treatment is to be directed.

The step of changing the spatial relationship between the patient and at least a part of the radiotherapy device may comprise moving the patient. For example, a patient positioning surface (or patient support surface), which supports the patient, may be moved. For example, the patient may be moved on or in relation to the patient positioning surface. However, in many cases the patient will be required to remain substantially static, relative to the patient positioning surface, to avoid any imaging or other steps having to be repeated, to accommodate a change in patient position.

The step of changing the spatial relationship between the patient and at least a part of the radiotherapy device may comprise moving one or more parts of the radiotherapy device. For example, it may comprise moving a rotatable member such as a gantry, or apparatus that connects to the gantry, relative to the patient.

The method may comprise aligning an image of the patient to a focal point, wherein the focal point comprises the reference location. The method may further comprise determining an offset between a location of the focal point and a location of an isocentre of a the treatment beam that is to be used to treat the patient, and changing a spatial relationship between the patient and at least a part of the radiotherapy device, according to the determined offset.

The focal point may have a location that coincides with a location of an isocentre of a first treatment beam, having a first identity, wherein the first treatment beam can be output by the radiotherapy device but is not intended to be used to treat the patient. The method may, in such a scenario, comprise determining an offset between the location of the isocentre of the first treatment beam and a location of an isocentre of a second treatment beam, having a second, different identity, and which comprises the identified treatment beam that is to be used to treat the patient, and changing a spatial relationship between the patient and at least a part of the radiotherapy device, according to the determined offset.

The method may comprise aligning an image of the patient to an isocentre of a first treatment beam, having a first identity, wherein a location of the isocentre of the first treatment beam comprises the reference location. The method may further comprise determining an offset between the location of the isocentre of the first treatment beam and a location of an isocentre of a second treatment beam, having a second, different identity, wherein the location of the isocentre of the second treatment beam isocentre comprises the isocentre location for the treatment beam that is to be used to treat the patient, and changing a spatial relationship between the patient and at least a part of the radiotherapy device, according to the determined offset.

The method may comprise obtaining a pre-treatment image of the patient. This may be done as an initial step. The pre-treatment image may be aligned or calibrated to the reference location. The method may comprise determining one or more movements of the patient (and/or of a patient positioning surface or patient support surface, on which the patient is supported) in order to align, or match, the patient's position in the pre-treatment image with a patient position in one or more reference images. The reference location may comprise a focal point of said one or more reference images.

The pre-treatment image may be aligned or calibrated to an isocentre of a reference beam. The method may comprise obtaining a reference image of the patient. A pre-treatment image, and/or a current position of the patient, may be aligned or calibrated to the reference image.

The method may comprise, before carrying out the above-described steps for this aspect, obtaining a location of a first isocentre, of a first treatment beam, obtaining a location of a second isocentre, of a second, different treatment beam, and determining a relative location between the first and second isocentres. The first and second treatment beams will have first and second respectively different identities. That is; the first beam will have at least one characteristic that differs from at least one characteristic of the second beam.

The location of the first isocentre may comprise the reference location and the location of the second isocentre may comprise the isocentre location for the treatment beam that is to be used to treat the patient. The offset may thus be determined according to the relative location (or spatial relationship) between the first and second isocentres. It may be referred to as an 'isocentre offset'.

The method may comprise obtaining an updated location of the first isocentre and/or of the second isocentre and determining an updated relative location between the first and second isocentres. The method may not necessarily require the location of the second isocentre to be updated every time the location of the first isocentre is updated, or vice versa.

The method may comprise, before carrying out the above-mentioned steps; obtaining an image of the patient and obtaining a location of a focal point of that image, obtaining a location of the beam isocentre for each of a plurality of treatment beams, having different respective identities, which can be output by the radiotherapy device, and determining a relative location between each of the beam isocentres and the focal point of the image. The image may be a reference image, which was used to help compile a patient-specific treatment plan for the patient.

The positioning of a patient for radiotherapy treatment using a radiotherapy device, according to this aspect, may be carried out before radiotherapy treatment commences or during radiotherapy treatment. It may be carried out during a pause in radiotherapy treatment.

The positioning of a patient for radiotherapy treatment may need to be updated or repeated to accommodate an upcoming change such as a change in the intended beam that is to be used for treating the patient and/or a change in the location and/or in the nature of a target region or sub-region that is to be treated by a radiotherapy treatment beam.

The step of changing a spatial relationship between the patient and at least a part of the radiotherapy device may comprise adding a first determined offset to a second, different, offset to produce a combined offset, and changing a spatial relationship between the patient and at least a part of the radiotherapy device according to the combined offset. The second, different offset may have been determined according to a calibration process or according to another process for calculating a patient position that is required for another particular purpose.

The method may comprise receiving an instruction to obtain an updated location of the first isocentre, and obtaining an updated location of the first isocentre, in response to that instruction. This may be an automated or semi-automated process, or it may require some user input. A radiotherapy device may be configured not to function, or to limit its function, until the updated location of the first isocentre has been obtained.

According to an aspect, a method is provided of determining a positioning for a patient for radiotherapy treatment using a radiotherapy device. The method comprises determining an identity of a treatment beam that is to be used to treat the patient, determining an offset between a reference location and an isocentre location for the identified treatment beam that is to be used to treat the patient, and determining a change in spatial relationship, between the patient and at least a part of the radiotherapy device, according to the determined offset. A patient may subsequently be moved, and/or a part of a radiotherapy device may be moved or altered, in accordance with the determined offset.

According to an aspect, a radiotherapy system is provided comprising a radiotherapy device comprising a treatment apparatus for providing a radiotherapy treatment beam and a controller configured to perform the method of any of the above-described aspects.

The radiotherapy system may be configured to deliver radiation in each of a coplanar configuration and at least one non-coplanar configuration.

The method according to one or more of the above-described aspects may be executed by a computer.

According to an aspect, a computer readable storage medium is provided, comprising computer-executable instructions which, when executed by a computer, cause the computer to carry out the method of any of the above-described aspects.

Although certain aspects above and examples or embodiments below may be described in isolation, it should be understood that any combination of aspects, examples and embodiments is contemplated, except when explicitly described as being mutually exclusive to one another.

FIGURES

Specific embodiments are now described, by way of example only, with reference to the drawings, in which:

FIG. 1 shows an Image Guided Radiotherapy (IGRT) device comprising a treatment apparatus and an imaging apparatus.

FIGS. 2*a*-2*d* show rotation of the IGRT device of FIG. 1.

Figure 3:
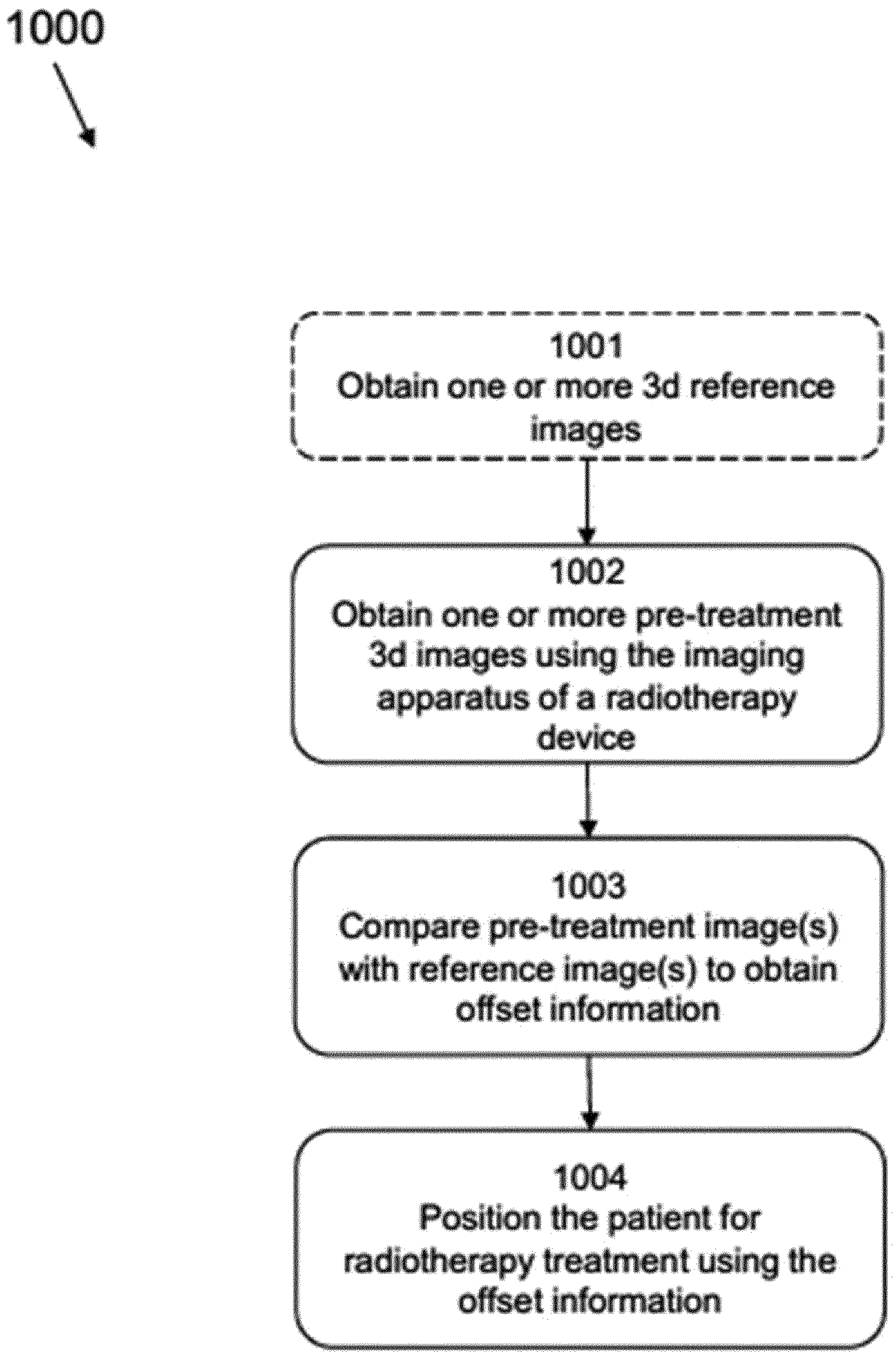

FIG. 3 is a flowchart showing an IGRT workflow.

Figure 4A:
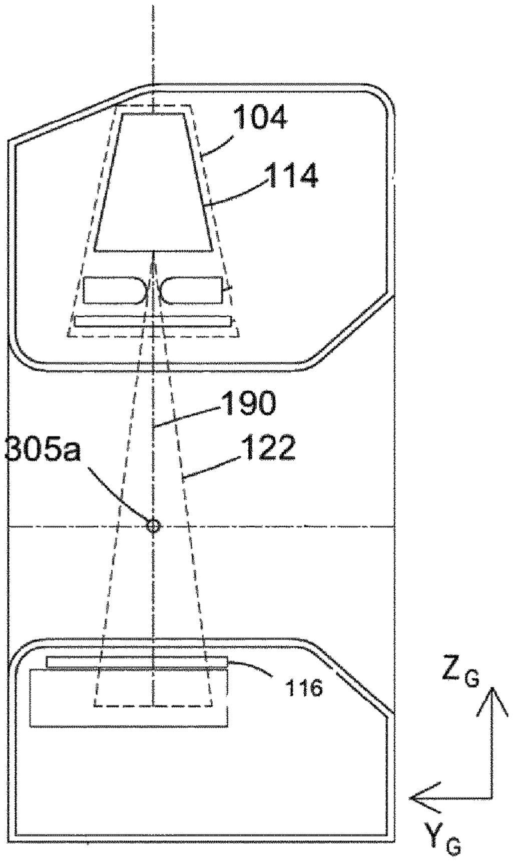
Figure 4B:
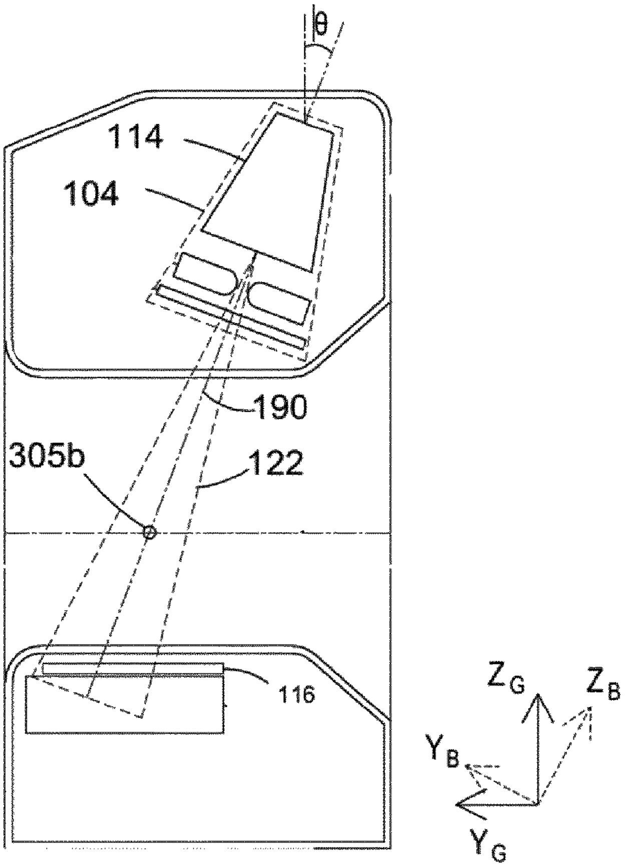

FIGS. 4*a*-4*b* depict embodiments of the apparatus in which the apparatus is in a coplanar and a non-coplanar configuration.

Figure 5:
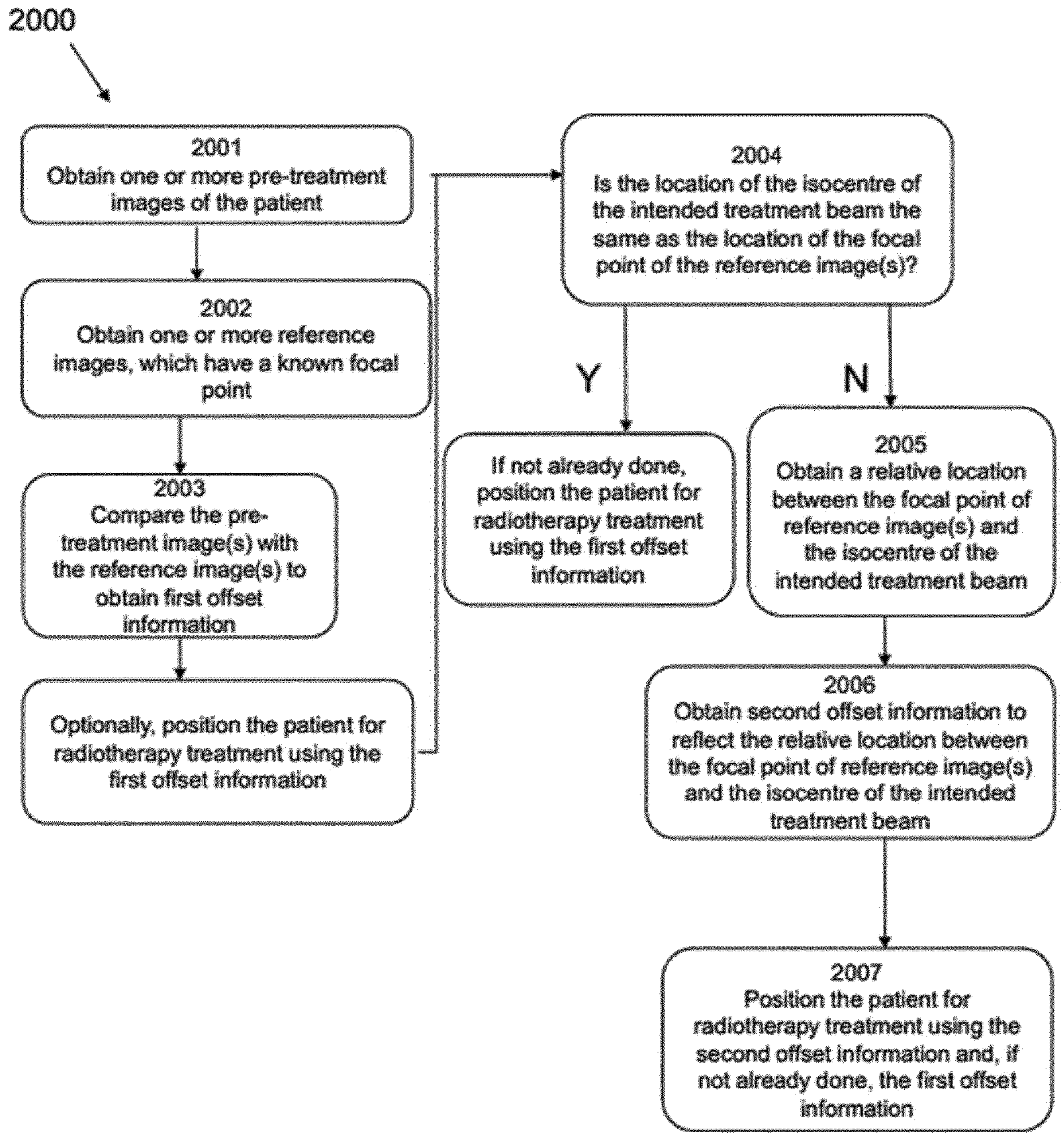

FIG. 5 is a flowchart showing an improved IGRT workflow.

DETAILED DESCRIPTION

FIG. 1 shows an Image Guided Radiotherapy (IGRT) device 100. The IGRT device 100 comprises a rotatable gantry 102 to which are affixed a treatment apparatus 104 and an imaging apparatus 106. In this example, the treatment apparatus 104 and the imaging apparatus 106 are attached to the gantry 102, so that they are rotatable with the gantry 102, i.e. so that they rotate as the gantry 102 rotates. Positioned generally along an axis 'X' central to the gantry is a table 110 upon which a patient 112 lies, for radiotherapy treatment. The table 110 may be referred to as a 'patient positioning surface' or as a 'patient support surface'.

Three gantry directions $X_G$, $Y_G$, $Z_G$ can be defined, where the $Y_G$ direction is perpendicular with an axis around which the gantry 102 rotates. The axis of rotation of the gantry 102 may be labelled $X_G$. When a patient is positioned for treatment by device 100, the gantry rotation axis $X_G$ may coincide with the patient longitudinal axis. The $Z_G$ direction extends from a point on the gantry corresponding to the treatment apparatus, towards the axis of rotation of the gantry. Therefore, from the patient frame of reference, the $Z_G$ direction rotates around as the gantry rotates.

The treatment apparatus 104 is configured to direct a treatment beam of therapeutic radiation towards a treatment volume of the radiotherapy device 100. The treatment apparatus 104 comprises a treatment beam source 114 and a treatment beam target 116. The treatment beam source 114 is configured to emit or direct therapeutic radiation, for example MV energy radiation, towards the patient 112. As the skilled person will know, the treatment beam source 114 may comprise an electron source, a linac (linear accelerator) for accelerating electrons toward a heavy metal, e.g.

tungsten, target to produce high energy photons, and a collimator configured to collimate the resulting photons and thus produce a treatment beam. For reasons of clarity and brevity, these components are collectively referred to as the treatment beam source 114. Once the treatment radiation has passed from the treatment beam source 114 and through the patient 112, the radiation continues towards treatment beam target 116, where it is blocked or absorbed. The treatment beam target 116 may include an imaging panel (not shown). The treatment beam target 116 may therefore form part of an electronic portal imaging device (EPID). EPIDs are generally known to the skilled person and will not be discussed in detail herein.

As explained further below, the radiotherapy device 100 may be configured to deliver both coplanar and non-coplanar (also referred to as tilted) modes of radiotherapy treatment. In coplanar treatment, radiation is emitted in a plane which is perpendicular to the longitudinal axis of the patient. In non-coplanar treatment, radiation is emitted at an angle which is not perpendicular to the longitudinal axis of the patient. In order to deliver coplanar and non-coplanar treatment, the treatment apparatus 104 can move between at least two positions or 'planar configurations', one in which the radiation is emitted in a plane which is perpendicular to the longitudinal axis of the patient (coplanar configuration) and one in which radiation is emitted in a plane which is not perpendicular to the longitudinal axis of the patient (non-coplanar configuration).

In the coplanar configuration, the treatment apparatus 104 is positioned to rotate about a rotation axis and in a first plane. In the non-coplanar configuration, the treatment apparatus 104 is tilted with respect to the first plane such that a field of radiation produced by the treatment apparatus 104 is directed at an oblique angle relative to the first plane and the rotation axis. In the non-coplanar configuration, the treatment apparatus 104 is positioned to rotate in a respective second plane parallel to and displaced from the first plane. The radiation beam is emitted at an oblique angle with respect to the second plane, and therefore as the treatment apparatus 104 rotates the beam sweeps out a cone shape.

The imaging apparatus 106 comprises an imaging beam source 118 and an imaging panel 120. The imaging beam source 118 is configured to emit or direct imaging radiation, for example X-rays and/or kV energy radiation, towards the patient 112. As the skilled person will know, the imaging beam source 118 may be an X-ray tube or another suitable source of X-rays. The imaging beam source 119 is configured to produce kV energy radiation. Once the imaging radiation has passed from the imaging beam source 118 and through the patient 112, the radiation continues towards the imaging panel 120. The imaging panel 120 may be referred to as a radiation detector, or a radiation intensity detector. The imaging panel 120 is configured to produce signals indicative of the intensity of radiation incident on the imaging panel 120. In use, these signals are indicative of the intensity of radiation which has passed through the patient 112. These signals may be processed to form an image of the patient 112. This process may be described as the imaging apparatus 106 and/or the imaging panel 120 capturing an image. By capturing two-dimensional (2D) images at multiple angles around the patient, and combining them, it is possible to produce a 3D image of the patient, for example using tomographic reconstruction techniques.

In FIG. 1, the treatment apparatus 104 and the imaging apparatus 106 are mounted on the gantry 102 such that a treatment beam travels in a direction that is generally perpendicular (i.e. at right angles) to that of the imaging beam. However other relative positions of treatment apparatus and imaging apparatus are contemplated.

Figure 2A:
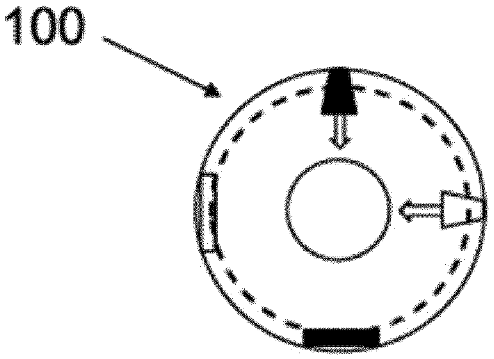
Figure 2B:
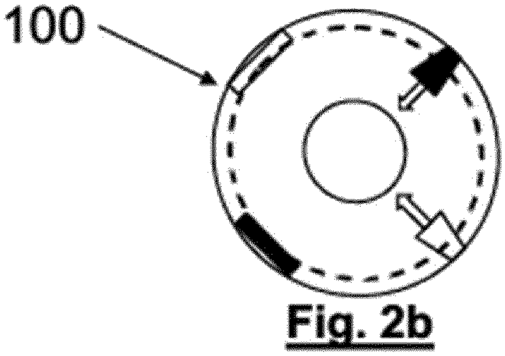
Figure 2C:
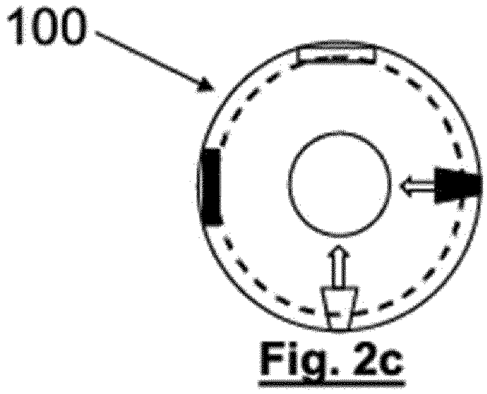
Figure 2D:
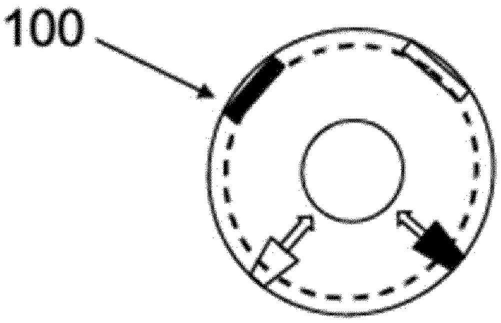

Because the gantry 102 is rotatable, the treatment beam can be delivered to a patient from a range of angles. Similarly, the patient can be imaged from a range of angles. This is illustrated in FIGS. 2*a* to 2*d*, each of which shows the gantry 102 of FIG. 1 at a different respective rotation angle, with each of FIGS. 2*b* to 2*d* showing the gantry at a 45 degrees clockwise rotation as compared to the immediately preceding figure (i.e. FIGS. 2*a* to 2*c*, respectively). These positions are illustrative only. The skilled person will know that the gantry 102 can be rotated to any of a number of discrete angular positions, relative to a patient. The treatment apparatus 104 may direct radiation toward the patient at one or more of those discrete angular positions, according to a treatment plan. The treatment apparatus 104 may even be used to continuously irradiate a patient at all rotation angles, whilst it is rotated by the gantry 102. The angles from which radiation is applied, and the intensity and shape of the therapeutic beam, may depend on a specific treatment plan pertaining to a given patient.

When a target region, which may comprise a tumour, within the body or skin of a patient is to be treated using the radiotherapy device 100, a clinician will position the patient 112 on the table 110. The device 100 is configured to implement a treatment plan, which may for example describe the various angles at which radiation should be directed toward the patient, the duration of each beam, the beam shape, etc. in order to achieve a desired dose distribution. The treatment plan may also call for beams of different energies or different characteristics to be used during the same treatment session in order to optimally meet the required dose distribution. The creation of a treatment plan is discussed in more detail, later in the present application.

In this way, the target region is irradiated at each gantry rotation angle, and thus will receive a relatively high dose of radiation. Areas of healthy tissue surrounding the target region will also briefly be irradiated, at times at which the treatment beam passes therethrough. But the rotation of the gantry will ensure that each area of healthy tissue is irradiated as little as possible, with each only being irradiated at certain angles of rotation. Unlike the target region, a particular area of healthy tissue will not be irradiated from multiple angles, and therefore will receive a reduced (and safe) dosage of radiation relative to the target region. Therefore, by correctly configuring the IGRT device 100 and correctly positioning the patient 112, accurate irradiation of the target region can be performed while irradiation of healthy tissue surrounding the target region can be minimised.

Reference is made herein to the 'isocentre' of the treatment apparatus 104 of the radiotherapy device 100. The isocentre may be described as a location in space that the treatment beam passes through at all gantry rotation angles. The therapeutic beam produced by the treatment beam source 114 may be conical, and in this case the isocentre may be described as the point or location in space through which the central (or axial) radiation beam, within a conical therapeutic beam, passes at all gantry rotation angles. In a hypothetical 'ideal system', the isocentre is a point in space. However, due to real-world effects such as small mechanical movements or flexes, for example flexes in a connecting arm via which the treatment beam source 114 is connected to the gantry, the isocentre may actually be defined by a small region, area, or volume in space. For example, it may be regarded as being a virtual sphere.

As mentioned above, the imaging apparatus 106 can be used to create a 3D pre-treatment image of at least part of the patient 112, which incorporates the target region. Based on this 3D pre-treatment image, and a knowledge of the location of the treatment beam isocentre, a clinician can identify a projected position of the treatment beam isocentre, relative to the target region. The table 110 supporting the patient 112 can then be moved, and/or another component of the radiotherapy device 100, such as the gantry 102, may be moved, as necessary, to ensure proper positioning of the target region, relative to the isocentre.

It will therefore be understood that the location of the treatment beam isocentre, relative to the patient and (in many cases) relative to (possibly three-dimensional) pre-treatment images produced by the radiotherapy device, should be known, in order to enable accurate radiotherapy treatment of a target region within the patient's skin or body. In order to correctly configure the apparatus and position the patient for radiotherapy treatment, targeting the target region(s) and minimising exposure of healthy tissue to radiation, the location of the treatment beam isocentre should be known to a high degree of accuracy.

As described in the background section above; it is typical for a first set of reference images to be obtained, often a few days or even weeks before radiotherapy treatment is due to commence, wherein a patient's patient-specific treatment plan can be devised, at least in part, based on those reference images. The reference images are typically taken by imaging equipment that is distinct from a radiotherapy device, however there are some radiotherapy systems that also include suitable imaging equipment for obtaining reference images. For example, reference images may be taken on a CT scanner.

When a treatment plan is being created, typically the treatment planning system (TPS) assumes that the 'isocentre' (or focal point) of the reference image(s)—which is the point around which the treatment plan is focused—will be coincident with the isocentre of the treatment beam of the radiotherapy device, during treatment. The isocentre of the reference image(s) may be a tumour or other target region, such that the aim of the treatment plan is to target the isocentre of the treatment beam at the tumour or other target region, at all times during radiotherapy treatment. However, the skilled reader will be aware that there are exceptions to this—for example, a tumour's location within a patient's anatomy may make it physically impossible for it to be always at the treatment beam isocentre. For example, if the tumour is located at one side of the patient, for example in a lung, it may not be practical to position the patient so as to have the tumour at the treatment beam isocentre at all times, during rotation of the gantry around the patient. In such a case, the treatment plan can determine that another point in the patient's anatomy is the focal point of the reference image(s), and thus is to be located at the treatment beam isocentre. The treatment beam can then prescribe that suitably positioned components such as barriers and apertures, for example leaves of a multi-leaf collimator (MLC), should be configured to divert the beam's path in a suitable manner, so that it is targeted at the tumour and not at its beam isocentre.

The treatment plan is created in order for its delivery to cause irradiation of tissue, via the delivery of specified doses according to a specified regime, at particular anatomical points within the patient's body, whose positions are identified with respect to the isocentre of the reference image (and, therefore, are identified with respect to the location of the isocentre of the radiotherapy treatment beam). A treatment planning system (TPS) necessarily needs to use a single location, as the location (or position) of the 'isocentre' of the treatment beam of the radiotherapy device, in order to have a consistent reference point when creating a treatment plan to treat a tumour or other region. The location of the isocentre that a TPS uses for this purpose will typically be the isocentre location for one of the treatment beams that the radiotherapy device can output. This beam may be referred to as a 'reference beam'. Its isocentre may be referred to as a 'reference isocentre'.

It is also typical for a set of 'pre-treatment' images to be taken, immediately or very shortly before the radiotherapy treatment is due to commence, in order to guide the radiotherapy treatment, for example to guide correct positioning of the patient. As is known to the skilled person; in order to make the radiotherapy treatment as effective as possible, the pre-treatment images should be aligned with the reference images, on which the treatment plan is based, and additionally should be aligned with the treatment beam isocentre.

FIG. 3 shows a flowchart of a known IGRT workflow 1000. Such a workflow may be referred to as a 'registration' process, wherein pre-treatment images of at least part of a patient, obtained immediately (or very shortly) before radiotherapy treatment are registered to previously-obtained reference images, of at least part of the patient. This workflow may also be referred to as being part of a 'calibration' process.

At step 1001, one or more reference images are obtained. The images are 3D, in this example. The images are of a patient who is to undergo radiotherapy treatment. They may be images of the whole patient or part of the patient that includes a target region or target regions. These reference images may be taken on a CT scanner and thus may have a high quality and high resolution. These images may form the basis of a radiotherapy treatment plan. These reference images may be taken some time before the radiotherapy treatment is to occur. As detailed hereabove, the patient's treatment plan may have been created, based on these references images, wherein the treatment plan adopts an assumption that the location of the 'isocentre' (or focal point) of the reference images, around which the treatment plan is based, is the same as the location of the isocentre of a 'reference' treatment beam, which can be output by the radiotherapy device.

At step 1002, one or more pre-treatment images are obtained using the imaging apparatus of a radiotherapy device. The images are 3D. These images may be referred to as IGRT images. These images are taken shortly before treatment is to commence. They are, in this example, taken by imaging apparatus that is comprised within the same radiotherapy device as the treatment apparatus, which is to provide the radiotherapy treatment to the patient. Therefore, the patient may be in place, on a patient positioning surface, awaiting treatment, when the pre-treatment images are taken. The pre-treatment images may therefore be used to position the patient on the day of treatment. The imaging apparatus of the radiotherapy device may, for example, comprise a kV imaging source. Cone beam computed tomography (CBCT) techniques may be used to produce these images.

Like the reference images, mentioned above; the pre-treatment images are also calibrated, or aligned, to an isocentre of a reference treatment beam, which can be output by the radiotherapy device. The reference treatment beam, the isocentre of which is used to align the pre-treatment images, should be the same as the reference treatment beam, the isocentre of which is assumed as the isocentre (or focal point) of the previously-captured reference images. For the pre-treatment images, a calibration map may be used, to guide the compilation of a plurality of two-dimensional images into a three-dimensional pre-treatment image, wherein the relative positioning of the two-dimensional images takes account of, inter alia, the location of the isocentre of the reference treatment beam.

At step 1003, the pre-treatment image(s) are compared with the one or more reference image(s). The two sets of images (i.e. the pre-treatment images(s) and the reference image(s)) are then aligned with one another, to get the patient into a correct position for treatment, in accordance with the treatment plan. For example, suitable features of the patient's anatomy, which can serve as landmarks, may be used to align the patient's position in the pre-treatment images with the position in the reference images, on which the treatment plan was based. Offset information is obtained, which accounts for any difference in position or location of the landmarks, between the two sets of images. This offset information may be a three dimensional vector which indicates a movement or 'shift' that is required in order to align the pre-treatment images with the reference images. There may be more than one three dimensional vector required, for different respective landmarks or for moving different respective parts of the patient's anatomy, to get him or her into a position that matches the position on the reference images, which form the basis of the patient's treatment plan. This process is known as registration and the skilled person in the field of radiotherapy will be familiar with registration techniques.

In an example, a clinical user (with the aid of IGRT software) superimposes a 3D pre-treatment image obtained by the imaging apparatus of the radiotherapy device at step 1002 onto a 3D CT scan (or 'reference image') of the patient, taken at step 1001 (and used to determine the patient-specific treatment plan). When the pre-treatment image is perfectly superimposed on the reference image, the software calculates how much the IGRT image had to be moved and in which direction(s). This may be calculated as a vector offset. The software, possibly with input from the clinician, can then calculate how the patient should be moved, relative to the radiotherapy apparatus of the radiotherapy device, in order to emulate the movement of the pre-treatment image and thus achieve alignment between the patient's position for radiotherapy treatment with his or her reference scans. The software can then create instructions, to be sent to the radiotherapy device, to realise that movement. Usually this will comprise sending instructions to the patient positioning surface, to move it and thus to move the patient.

At step 1004, the patient is positioned for radiotherapy treatment using the calculated offset information. Typically, the patient positioning surface is re-positioned according to the offset but it may be that one or more parts of the radiotherapy device is moved, to achieve the desired patient positioning. Once, the patient is positioned correctly, the treatment beam generated by the radiotherapy device can be directed at the target region or regions of the patient's anatomy, as required by the treatment plan.

Although many current radiotherapy devices are known to be very effective; improving the accuracy of radiotherapy treatment, to target tumours or other target regions even more effectively, and to better shield healthy tissue from potentially harmful radiation, is nonetheless an ongoing goal. Both clinicians who use radiotherapy devices and manufacturers who make them are keen for improvements to be made, even to radiotherapy devices that are already highly effective. Of course, while obtaining any such improvements, it is desirable to maintain efficiency, both for the manufacturer and the user, and not to add undue complexity, cost or bulk to a radiotherapy device.

Many aspects of a radiotherapy device and its processes potentially have an effect on the accuracy of its operation. Referring to the above-described workflow of FIG. 3 by way of example; one aspect that can impact accuracy is quality of the 3D pre-treatment images that are produced at step 1002.

As mentioned briefly above and as described in more detail in co-pending GB application no. 1918426.6, in the name of Elekta Limited, a 3D pre-treatment scan is usually comprised of a plurality of 2D scans, taken at different respective angles of rotation of the gantry, and combined with one another. The manner in which those 2D images are combined can be improved, for example by considering real-world effects such as flexing or sagging of parts of the radiotherapy device during rotation, which can affect the relative positions of the imaging apparatus and the patient.

As recognised by the present inventors, another aspect that can impact accuracy of the radiotherapy treatment that is deliverable by a radiotherapy device is the accuracy with which any images of the patient that are used to guide subsequent radiotherapy treatment, are calibrated or aligned with the isocentre of the treatment beam that is to be used. For example, for an IGRT radiotherapy device, the pre-treatment images should be accurately calibrated or aligned with the treatment beam isocentre, in order to ensure optimal patient positioning for treatment.

The present inventors have recognised that pre-existing techniques for positioning a patient for radiotherapy treatment may be sub-optimal, because they assume a single reference position for the isocentre of every treatment beam of a radiotherapy apparatus. As discussed above, both the creation of a patient-specific treatment plan, based on reference images of a patient, and the compilation of a three-dimensional pre-treatment image from a plurality of two-dimensional images, taken of the patient shortly before radiotherapy treatment, assume a particular location (or position) of the isocentre of the treatment beam of the radiotherapy apparatus. The assumed location of the isocentre of the treatment beam will typically be correct, for one of the treatment beams that is deliverable by the radiotherapy apparatus. However, the present inventors have recognised that the location (or position) of the treatment beam isocentre will not necessarily be the same for all available treatment beams, for a given radiotherapy device. That is; treatment beams of different respective energies, and/or treatment beams of the same energy but that have different filters applied thereto (or one of which has a filter and another of which is filter-free) and/or treatment beams of the same energy but delivered from planar and non-coplanar configurations may have (and, in practice, commonly do have) different respective locations of beam isocentre.

The above being the case; if a patient is positioned using images that have been compiled, calibrated, or aligned, based on the isocentre position of a 'reference' treatment beam of a first type (or identity), which has a corresponding first isocentre location, but the patient is subsequently actually treated using a treatment beam of a second, different type (or identity), which has a corresponding second, different isocentre location, there may be a systematic mispositioning of the target region or regions, within the patient's anatomy, with respect to the isocentre of the second beam. This can lead to a reduction in accuracy of the radiotherapy treatment.

The difference in isocentre location, for different beams that can be output by the same radiotherapy treatment apparatus, may be due, for example, to minute differences in the currents that are supplied to the respective beam steering magnets for each beam. Other contributing factors may include the fact that beams of higher energies need higher magnetic fields from the steering magnets to be generated, in order to steer those beams, and that the power supplied to the bending/steering magnets must typically be increased for higher energies of electron beam, within the treatment beam generation components of a radiotherapy device. Although the resulting differences between isocentre locations for different respective treatment beams may be considered to be small; the present inventors have recognised that they nonetheless may have an impact on the accuracy of the radiotherapy treatment that a radiotherapy device can provide.

In some implementations, a difference in isocentre location may result from a change in the planar configuration of the treatment apparatus 104. A change in the planar configuration of the treatment apparatus 104 may comprise a switch from a coplanar configuration to a non-coplanar configuration, as outlined below.

During radiotherapy treatment, it is desirable to deliver radiation from multiple angles. One method of achieving this is through rotating the treatment apparatus 104 about a patient, for example about a longitudinal axis of the patient, such that the radiation can be delivered to the patient from multiple angles. Treatments that employ rotation of the treatment apparatus 104 in this manner are known as coplanar, and radiotherapy devices can deliver this treatment while being in a coplanar configuration. A further degree of freedom is achieved by tilting the radiation source outside of the plane perpendicular to the patient's longitudinal axis, such that radiation is delivered at an oblique angle relative to the longitudinal axis. Non-coplanar radiotherapy thereby applies radiation from a number of positions, which do not all share the same geometric plane relative to the patient. This non-coplanar configuration helps increase the number of angles at which radiation can be delivered to the patient, thereby minimising the effect on healthy tissue.

However, the tilting of the treatment apparatus 104 from a coplanar configuration to a non-coplanar configuration can result in a change in location of the beam isocentre, as outlined through FIG. 4*a* and FIG. 4*b*.

FIG. 4*a* illustrates the radiotherapy device in a coplanar mode, or configuration, while FIG. 4B illustrates the radiotherapy apparatus in a non-coplanar (or tilted) mode, or configuration. Features of FIG. 4*a* and FIG. 4*b* may have equivalent or similar properties to the corresponding features of the radiotherapy device as described in FIG. 1.

In both FIG. 4*a* and FIG. 4*b*, the treatment apparatus 104 emits a radiation beam 122 along a beam axis 190, where the beam axis 190 may be used to define the direction in which the radiation is emitted by the treatment apparatus 104. The beam axis 190 may be defined as, for example, a centre of the radiation beam 122 or a point of maximum intensity. The beam axis 190 intersects an axis of rotation of the gantry at or near the isocentre 305*a*/305*b*.

Three beam directions $X_B$ $Y_B$ $Z_B$ can be defined, where the $Z_B$ direction corresponds to the beam axis 190. In the coplanar configuration of FIG. 4A, the beam directions $X_B$ $Y_B$ $Z_B$ correspond to the gantry directions $X_G$ $Y_G$ $Z_G$, and the beam axis 190 may pass through the beam isocentre 305*a*. Typically, a beam in a coplanar configuration may be taken as a reference beam for image capture, calibration and/or alignment, and an actual isocentre position for radiotherapy treatment.

In the coplanar configuration, the treatment apparatus 104 is configured to rotate in a first plane of rotation, e.g. a first sagittal plane. This first plane of rotation passes through the isocentre 305*a*. The treatment apparatus 104 is positioned such that the beam axis 190 is coplanar with the first plane of rotation.

In the non-coplanar configuration of FIG. 4*b*, the treatment apparatus 104 is in a different position and orientation relative to the coplanar mode of FIG. 4*a*. Compared to the coplanar mode, in the non-coplanar mode the treatment apparatus is both tilted (e.g. rotated) and translated relative to the gantry 102. Thus, the beam directions $X_B$ $Y_B$ $Z_B$ do not correspond to the gantry directions $X_G$ $Y_G$ $Z_G$. The $Y_B$ $Z_B$ directions are rotated relative to the $Y_G$ $Z_G$ directions by an angle θ, corresponding to the change in the angle of the treatment apparatus 104.

In the non-coplanar configuration, the treatment apparatus 104 is positioned to rotate in a respective second plane of rotation which is parallel to and displaced from the first plane of rotation, e.g. a second sagittal plane displaced from the first plane by a distance in the $Y_G$ direction. In this configuration, the second plane of rotation is also displaced from the isocentre 305*b*.

Multiple different non-coplanar configurations may be provided, where the beam of radiation 122 is emitted at multiple different angles. Thus, multiple different beam identities are possible when in the treatment apparatus is identified as being in a non-coplanar configuration.

The translation and rotation of the treatment apparatus 104 in the non-coplanar configuration can result in a change in location of the isocentre of the beam—from location 305*a* in FIG. 4*a* to location 305*b* as shown in FIG. 4*b*. The change in angle θ of the treatment apparatus in the non-coplanar configuration results in radiation being emitted from the treatment apparatus at an angle which is not perpendicular to the axis of rotation. Thus, the isocentre of such a beam would be offset from the isocentre of a reference beam in a coplanar configuration by the angle θ. The offset between the respective isocentres of location 305*a* and location 305*b* may increase with an increase in the angle θ, corresponding to an increase in the angle of the treatment apparatus 104.

Thus, for two different available therapy beams, there are two different isocentres which need to be accounted for prior to radiotherapy treatment.

The present inventors have recognised that, by ascertaining the relative locations (which may instead be referred to as the 'relative positions' or as the 'spatial relationships') between the respective isocentres of its different available therapy beams, which have different respective identities or characteristics, a radiotherapy device or a radiotherapy system can account for any difference between a treatment isocentre position that is used as a reference position, for image capture, calibration and/or alignment, and an actual isocentre position for radiotherapy treatment. This can be done in a streamlined manner, and can improve the accuracy of the radiotherapy treatment that is deliverable by the radiotherapy device. Therefore any target areas within a patient's anatomy can be irradiated more effectively and any healthy tissue is shielded more effectively from unnecessary irradiation.

Thus, a method is provided herein of positioning a patient for radiotherapy treatment using a radiotherapy device; wherein that method accounts for any difference between the location (or position) of an isocentre of a treatment beam of a first identity, with which a patient, or an image of the patient (such as a pre-treatment image and/or a reference image, on which a treatment plan has been based), has been aligned, calibrated or registered, and the location (or position) of an isocentre of a treatment beam of a second, different identity, with which the patient is to be treated. The identity of a treatment beam may be defined by its energy, at which the treatment beam would be delivered to the patient, and/or by other characteristics such as the profile of the beam, whether or not it is filtered and, if filtered, the nature of the filter.

As described in relation to FIGS. 4*a* and 4*b*, the identity of a treatment beam may also be defined by the angle at which it would be delivered to the patient, for example with respect to the longitudinal axis of the patient and/or with respect to the gantry rotation axis, or with respect to a plane perpendicular to either of these axes. Equivalently, the identity of a treatment beam may be defined by the configuration, or mode, of the device at the time of delivery of the beam, for example whether the device is in a coplanar configuration or whether the device is in a non-coplanar configuration. Beams delivered while the device is in a coplanar configuration may be referred to as coplanar beams, and beams delivered while the device is in a non-coplanar configuration may be referred to as non-coplanar beams.

The present inventors have also recognised that reference images of a patient need not have their isocentres (or focal points) located exactly coincident with any of the treatment beam isocentres of a radiotherapy device. Instead, it is possible for the focal point of a reference image to be an arbitrary point, the location of which is accurately known, relative to the treatment apparatus of the radiotherapy device. In such a scenario, if the relative location is known, of each of the respective isocentres of the different treatment beams that a radiotherapy device can output, relative to the focal point of the reference images, a correction can then be made to the patient's location for radiotherapy treatment, based on an offset between the location of the focal point within the reference image and the actual location of the isocentre of the treatment beam that is to be used to treat the patient.

Similarly, the present inventors have recognised that pre-treatment images of a patient need not be calibrated to a particular treatment beam isocentre. Instead, it is possible for the focal point of a pre-treatment image to be an arbitrary point, the location of which is accurately known, relative to the treatment apparatus of the radiotherapy device. In such a scenario, if the relative location is known, of each of the respective isocentres of the different treatment beams that a radiotherapy device can output, relative to the focal point of the pre-treatment images, a correction can then be made to the patient's location for radiotherapy treatment, based on an offset between the location of the focal point within the pre-treatment image and the actual location of the isocentre of the treatment beam that is to be used to treat the patient.

The method enables improved accuracy of the subsequent radiotherapy treatment, by targeting a target region within the patient's anatomy more precisely and thus increasing the extent to which irradiation of any healthy tissue is avoided. At the same time, the method does not require computationally intensive or labour-intensive steps to be carried out, either by the user of the radiotherapy device (i.e. by the clinician) or by the software controlling the radiotherapy device, or indeed by the manufacturer. Indeed, the method can be implemented as an add-on to, or incorporated within, one or more pre-existing patient alignment or moving processes. This can be understood more fully with reference to FIG. 5.

FIG. 5 shows an improved method of positioning a patient for radiotherapy treatment using a radiotherapy device. It relates specifically to a radiotherapy device that is capable of delivering a plurality of different radiotherapy treatment beams, having different respective identities (or types)—for example, having different respective angles of delivery and/or energies and/or different respective filters or degrees of filtering—wherein the improved method accounts for the spatial relationships between the respective isocentres of treatment beams of different identities. The improved method 2000 may be carried out, or controlled, by a processor, computer or controller that is comprised within or is in communication with the radiotherapy device. For example, it may be carried out using IGRT software, running on a computer.

The improved method 2000 of FIG. 5 may be carried out instead of the method 1000 of FIG. 3. Alternatively, the improved method 2000 may be performed, starting at step 2004 therein, after all steps of the method 1000 of FIG. 3 have been completed. The improved method 2000 can be performed in isolation or as part of, or in conjunction with, any other suitable calibration or registration process, which prepares a radiotherapy device and/or positions a patient for subsequent radiotherapy treatment. The improved method 2000 may be an automated or a semi-automated method. Typically, the patient will already have had reference images taken (for example, CT images), on the basis of which a patient-specific treatment plan, comprising radiotherapy treatment and possibly other steps, will have been determined, before the improved method 2000 is performed.

Looking at the steps of the improved method 2000 in turn; at step 2001, one or more pre-treatment images are obtained. The images are of a patient who is to undergo radiotherapy treatment. They may be images of the whole patient and/or of part of the patient that includes a target region or target regions. The images are 3D. These images may be referred to as IGRT images. These images are typically taken just before treatment is to commence. Therefore, as described above, the patient may be located in situ within a radiotherapy device, awaiting treatment, when the pre-treatment images are taken. Cone beam computed tomography (CBCT) techniques may be used to produce the pre-treatment images. This step 2001 may comprise actually capturing the pre-treatment images, using the imaging apparatus of a radiotherapy device, or it may comprise retrieving pre-treatment images, which have already been captured.

At step 2002, one or more reference images of the patient, which were captured previously and which formed the basis of the patient's treatment plan, are obtained. As described above, the reference images will have an isocentre, or focal point, which may be coincident with the isocentre of one selected treatment beam, which is deliverable by the radiotherapy device, and which has a respective identity or unique set of characteristics. and. This isocentre may be referred to as a 'reference isocentre'. The location or position of the reference isocentre may be referred to as a 'reference position'. The selected treatment beam may be referred to as a 'reference treatment beam'.

Alternatively, the reference images may have an arbitrary focal point, which has a known location relative to the treatment apparatus (and/or to another aspect) of the radiotherapy device. In such a scenario, the relative locations between each of the isocentres of the different respective beams (which have different respective identities) that can be output by the radiotherapy device should be known—or should be established, before radiotherapy treatment—relative to the focal point of the reference images.

In the present example, the focal point of the reference images, is the isocentre of the lowest-energy treatment beam (for example, a 6 MV treatment beam). But having a focal point that coincides with of any of the available treatment beams, or having an arbitrary focal point in the reference images, is contemplated. Another embodiment, for example, may assign the focal point of the reference images to an isocentre of a treatment beam delivered while the treatment apparatus is in a coplanar configuration.

In this example, the location of the focal point of the reference images has been previously determined and stored, in a memory that is comprised within, or accessible to, the controller that is carrying out the improved method 2000. It may be possible, in some cases, for a controller to measure, or otherwise determine, the position or location of the focal point of the reference image(s) as part of the currently described improved method 2000. However, the skilled reader will appreciate that it is likely to be more efficient for it to be pre-recorded, so as not to waste time before the patient's radiotherapy treatment can commence.

The 'isocentre' of a treatment beam is, according to the improved method 2000, a point (or small volume) through which the treatment beam will pass, at all rotational angles of the gantry and at all rotational angles of the radiation head, on which the treatment apparatus is mounted. As detailed in co-pending GB application no. 1918426.6, in at least some cases, the actual location of the isocentre of any particular beam may vary during rotation of the gantry of the radiotherapy device, on which the treatment apparatus and/or the imaging apparatus are mounted. Such variation can cause the exact location of the isocentre, for a particular beam, to differ from a theoretical or 'ideal' location of that isocentre, due to real world effects, such as sagging or flexing of parts of the radiotherapy device. This variation, if present, may be accounted for during a calibration phase, before radiotherapy treatment commences. For example, a calibration map that determines how a plurality of 2D images should be combined to form a 3D pre-treatment image may take possible changes of isocentre location with gantry rotation into account. Therefore, the improved method 2000 may adopt an assumption that each treatment beam has a corresponding single respective location for its isocentre (or for a central point of its isocentre, if the isocentre is a small volume).

Returning to the improved method 2000 shown in FIG. 5; at step 2003, the pre-treatment image(s) is/are compared with the reference image(s) In particular, the location(s) of one or more landmarks within the patient's anatomy is/are compared within the two (sets of) images. Offset information is then obtained, which accounts for any difference in position or location, of those landmarks, between the pre-treatment image(s) and the reference image(s). This offset information may comprise a three-dimensional vector which indicates a movement or 'shift' that is required in order to position the patient to match his or her position for treatment with his or her position in the reference image(s). This offset information may comprise a six-dimensional vector (or a vector having up to six dimensions), as it may comprise rotational and translational components, describing required anatomical changes for getting the patient into position for treatment. In FIG. 5, this offset information, obtained at step 2003, is referred to as being 'first offset information'.

Once steps 2001 to 2003 have been completed, the controller may send instructions to the relevant parts of the radiotherapy system, to realise the movements/alterations that are required, according to the first offset information, in order to align the patient's position with the reference image(s). Alternatively, any such movements/alterations may be stayed, until the controller has carried out the other steps shown in FIG. 5, which are detailed below.

The present inventors have recognised that carrying out steps 2001 to 2003 may give rise to incomplete alignment between the patient and the radiotherapy treatment beam that will be used to treat him or her, if that treatment is to be carried out using a treatment beam for which the isocentre location is different to the location of the focal point of the reference image(s), on which the patient's treatment plan was based. Therefore, the present inventors have recognised that some additional steps should be taken. These are as follows:

At step 2004, a check is carried out to ascertain whether the location of an isocentre of the treatment beam with which the patient is to be treated (which may be referred to as an 'intended treatment beam') is the same as the location of the focal point of the reference image(s). For example, if the focal point of the reference image(s) coincided with the isocentre of a reference treatment beam, which can be output by the radiotherapy device, it is checked whether the intended treatment beam is the same as that reference treatment beam. This step 2004 is shown in FIG. 5 as occurring after steps 2001 to 2003 have been completed. In practice, this step 2004 may in fact be carried out before, or in parallel with, steps 2001 to 2003, at any suitable time.

If, as a result of step 2004, it is established that the treatment beam with which the patient will be treated has an isocentre location that is coincident with the focal point of the reference image(s), then it is determined that the patient will be correctly positioned, as a result of steps 2001 to 2003 (and subject to any other known calibration or registration processes). The controller may therefore, at that point, instruct the relevant parts of the radiotherapy system to be move/altered, based on the first offset, determined in step 2003. If, however, it is established at step 2004 that the patient is to be treated with a treatment beam, the isocentre of which is not coincident with the focal point of the reference image(s), then the improved method 2000 should advance to the further steps shown in FIG. 5, which are as follows:

At step 2005 a relative location (or position) is obtained, between the isocentre of the intended treatment beam and the focal point of the reference image(s). The location of the isocentre of the intended treatment beam may be referred to as the 'real' isocentre or the 'treatment' isocentre. The relative location may comprise a difference in a location of the focal point of the reference image(s) and a location of the real isocentre. The relative location may comprise a direction and/or a distance of the focal point of the reference image(s), away from the real isocentre. The relative location may comprise a direction and/or a distance of the real isocentre, away from the focal point of the reference image(s).

In this example, the locations of the isocentres for each of the available beams that can be output by the radiotherapy device, the relative locations between those isocentres (relative to one another), and the relative locations of each of those isocentres, relative to the focal point of the reference images, have been previously determined and stored, in a memory that is comprised within, or accessible to, the controller that is carrying out the improved method 2000. It may possible, in some cases, for a controller to measure, or otherwise determine, the locations (or positions) of the various isocentres as part of the currently described improved method 2000. However, the skilled reader will appreciate that it is likely to be more efficient for those locations to be pre-recorded, so as not to waste time before the patient's radiotherapy treatment can commence. Nonetheless, there may be requirements for one or more pre-recorded isocentre locations to be updated, for example periodically and/or after a pre-determined event or number of events have occurred. This is discussed in more detail, later in the present application.

At step 2006, second offset information is obtained, which reflects the relative location between the focal point of the reference image(s) and the real isocentre of the treatment beam that is to be used, to treat the patient. The second offset information may be a three-dimensional vector which indicates a movement or 'shift' that is required in order to align the focal point of the reference image(s) to the real isocentre. The skilled person will therefore appreciate that such a vector would also represent a movement or 'shift' that would enable an image, such as a reference image (and a patient who is being positioned to match his or her position in that reference image), which has been aligned to the focal point of the reference image, to be shifted in order to instead be aligned with the real isocentre of the treatment beam that is to be used, to treat the patient.

Step 2006 may comprise a software calculation of how much the pre-treatment image should be moved and in which direction(s), in order to align it with the real isocentre of the intended treatment beam, which is to be used for subsequent radiotherapy treatment. This may be calculated as a second vector offset. The software, possibly with input from the clinician, may then calculate how the patient should be moved, relative to the radiotherapy apparatus of the radiotherapy device. The software can then create instructions, to be sent to the radiotherapy device, to realise or action that movement. This may comprise creating instructions for the patient positioning surface, to move it and thus to move the patient, and/or it may comprise sending instructions to move or otherwise alter one or more other parts of the radiotherapy device or radiotherapy system.

At step 2007, the patient positioning surface and/or one or more other parts of the radiotherapy device or radiotherapy system are moved, in accordance with instructions received from the controller, in order to align the patient's position with the intended treatment beam. If the patient was not already moved as a result of steps 2001 to 2003, the movement at step 2007 may encompass the 'first' movement that was calculated as being required according to those steps, plus the 'second' movement calculated according to steps 2004 to 2006. The skilled person will understand how two movement vectors may be added, to arrive at a net movement vector.

In some cases, there may be other calibration or registration processes conducted, as part of a pre-treatment regime, and the controller may calculate a combined movement, that encompasses the movement(s) required according to the above-described improved method 2000 and one or more movements required according to one or more of those other calibration or registration processes. The movements may be combined using vector addition, which will be known to the skilled person, or using any other suitable calculation or process.

Those skilled in radiotherapy techniques will know that it is common for a patient to have more than one target region, which is to be targeted during a radiotherapy session. Moreover, a patient may have a large target region, or a target region that is difficult to treat, which requires the radiotherapy beam to be moved in order to target multiple different points (or sub-regions) within that target region. Furthermore, different target regions, or different sub-regions within a target region, may require respectively different treatment, for example they may need to be treated using different respective energies of treatment beam. Generally, a patient-specific treatment plan will encompass any requirements such as these, and will set out a regime that details the locations, within the patient's anatomy, that should be targeted, the length of time for which each location should be targeted and the characteristics of the treatment beam that should be used, including its required energy, angle, beam profile and any filters that should be adopted such as a beam flattening filter.

The improved method 2000 shown in FIG. 5 has been described above in relation to an initial set up of a patient, before a radiotherapy session commences. Therefore the target region described above may be regarded as being a first target region (or sub-region) that is to be targeted, according to the patient's treatment plan. However the improved method 2000 can also be applied to movements that are required during a radiotherapy session, in accordance with a treatment plan. For example, if a treatment beam is to be moved during a radiotherapy session, to target a second region or sub-region, the steps of FIG. 5 may be repeated, to align the second region or sub-region correctly, relative to the real isocentre of the intended treatment beam. The skilled reader will appreciate that, in such a scenario, the image or images that are obtained at step 2001 may not be pre-treatment images, but may be current or recent images, taken by the imaging apparatus of the radiotherapy device during the radiotherapy session.

It is also possible that a treatment plan will include changes between beams of different energies, of different angles or of different other characteristics, during a radiotherapy session. Again, the improved method 2000 may be re-applied each time there is to be a change of treatment beam identity, with the understanding that the images used in step 2001 may be images obtained during the course of treatment, as opposed to being pre-treatment images.

The process of obtaining the location of an isocentre of a treatment beam for a radiotherapy device will be well known to the skilled reader, and thus will be described herein only briefly. The position of the treatment beam isocentre may be determined by trial and error. According to one example, a ball-bearing phantom is placed at the expected position of the treatment beam isocentre (i.e. along the geometric centre of the gantry). Images of the ball bearing phantom are acquired using a radiation detector positioned opposite the source of MV radiation. This detector may form part of an electronic portal imaging system, for example. These images are acquired at multiple gantry rotation angles. This can enable the isocentric volume to be determined. The ball-bearing attenuates the MV radiation and thus impacts the intensity distribution of the radiation received at the detector. Therefore, from the images, it can be determined whether the ball-bearing phantom is positioned at the treatment beam isocentre. If the ball bearing is not positioned at the isocentre, then it is moved slightly. This process is repeated until the ball-bearing phantom coincides with the treatment beam isocentre.

Having positioned the ball-bearing phantom at the MV isocentre, it is then possible to determine the location of the isocentre in 3D images produced by the imaging apparatus of the radiotherapy device. The ball-bearing phantom is kept in place, and the imaging apparatus is then used to obtain 2D images at multiple gantry rotation angles. The location of the ball-bearing in the 2D images, and the resulting 3D image which may be constructed form the 2D images, indicates the position of the treatment beam isocentre in the images. These images would typically be taken at installation of a radiotherapy device in its radiotherapy environment and at periodic times thereafter, to ascertain if there have been any changes to the treatment beams that may affect their respective isocentre positions. Also, if any components or subsystems involved in the generation of the treatment beam have been changed or recalibrated, then this would likely impact the beam output and quality assurance (QA) would be needed to determine if the isocentre has changed as a result. Hospital departments (or other radiotherapy centres) would typically have a calendar of QA that needs to be performed with different periodic tests to run.

The improved method 2000 may be carried out on a device-by-device basis. Due to real world effects, the locations of the isocentres for various available treatment beams are not likely to be exactly the same in every radiotherapy device of the same type. Therefore the locations of the isocentres of the different available treatment beams (having different respective delivery angles and/or energies and/or other characteristics), and/or their relative locations, may be established and recorded for each device, during an initial set up or calibration process. The skilled reader will be familiar with such processes. Moreover, the locations of the isocentres may be checked or reacquired, during the life of the radiotherapy device.

It may be possible for the manufacturer and/or the programmer of the system controller and/or the user to set device-specific conditions, under which the location of an isocentre should be checked. Moreover, the controller and/or the radiotherapy device may be configured to enforce or require checking or reacquisition of one or more isocentre locations, under certain conditions, in order to ensure ongoing high levels of accuracy.

For example, a condition under which a user may choose to, or be required to, check the location of an isocentre position is when a particular beam has been recalibrated or subjected to a service check. After such a recalibration, the system may be configured (or configurable) to check the isocentre location for that beam, before any radiotherapy treatment can resume, or at least before any radiotherapy treatment using that beam can resume. It may be that QA indicates that only one beam needs to be adjusted after a specific service action. But even if multiple beams need to be recalibrated, they can be done one at a time.

For example, the system may be configured (or configurable) to check the isocentre location for one or more of the treatment beams after every radiotherapy treatment or after a pre-determined number of radiotherapy treatments, or after a combined pre-determined length of time of radiotherapy treatment, or periodically. For example, it may be deemed appropriate or necessary to check the location of the reference isocentre more often than certain other isocentres. For example, it may be deemed appropriate or necessary to check the isocentre location of a beam that is used most often, and/or of a beam that is known to be prone to isocentre shift, more often than certain other isocentres. The details of when it is deemed appropriate or necessary to check or verify the isocentre positions for different available treatment beams may vary between devices.

When a check or reacquisition of an isocentre location or locations is to be carried out, it can be done in a straight forward manner, and the new (or verified) isocentre location(s) can be stored in a memory comprised within, or accessible to, the controller. There is no need to update the isocentre locations for every beam, if the check has been carried out due to a requirement having arisen for just one of the beams. Instead, the isocentre location for the beam in question can be updated and the system can then (either automatically or with user input) adjust the relative locations between it and the other isocentre locations and between it and the location of the focal point of the reference image(s), if appropriate.

There is no need to involve any external devices or controllers, in order to acquire, check or reacquire the isocentre positions for the available treatment beams of a radiotherapy device, according to the improved methods described herein. Moreover, acquiring, checking, updating or changing the locations of one or more isocentres does not lead to other information needing to be changed. For example, co-pending GB application no. 1918426.6, describes the creation of a calibration map or 'flexmap' for combining 2D pre-treatment images to form a 3D image, which can be registered to previously-obtained reference images of a patient. Each flexmap is based on a single treatment beam, and thus on a single reference isocentre location. If there are multiple treatment beams available for a radiotherapy device, and/or if the treatment beam isocentre has to be changed or updated for one of those beams, the improved methods described herein ensure that there is no need to create an individual flexmap for each available beam, nor to update such a flexmap if an isocentre location is changed. Instead, a computationally fast and efficient process is followed, wherein the (new) location is stored for the/each beam, and the relative locations between each isocentre (or at least between the reference isocentre and each of the other isocentres) can be calculated, stored and updated as appropriate.

According to the improved methods described herein, there is no need for every available treatment beam to have a coincident isocentre. In fact, it is permissible for some or all of them to have different respective isocentre locations. Therefore, as mentioned above, the change of isocentre location for one beam need not give rise to the need for an isocentre adjustment for any of the others. This avoids the complicated manipulation of beam steering properties that would otherwise have to be undertaken, if two or more isocentre were required to coincide with one another.

By accounting for the fact that different treatment beams will have different respective isocentres, and enabling repositioning of a patient prior to and/or during radiotherapy treatment, to account for those differences, potential systematic offsets that could otherwise be present in radiotherapy treatment delivery are avoided. Although the difference(s) in isocentre location between beams of different respective delivery angles and/or energies and/or different profiles and/or different respective other characteristics may, at least in some cases, be relatively small; anything that further improves the accuracy of radiotherapy treatment that is deliverable by a radiotherapy device is welcome and beneficial. This is particularly the case because the overall performance of radiotherapy devices continues to improve, with other (previously-encountered) sources of error diminishing and thus exposing smaller variations that still exist. Moreover, because the improved methods described herein enable enhanced accuracy to be provided in a straight forward, computationally-efficient, streamlined and cost-effective manner, they are highly desirable and provide net benefit to the manufacturer, purchaser and user of a radiotherapy device, as well as to the patients who will receive the resulting improved radiotherapy treatment.

The improved methods described herein enable the margins of the treatment beam (i.e. the size of an area that the beam irradiates, at any given time) to be reduced and restricted, thus further protecting healthy tissue surrounding a target region from unnecessary irradiation. This is because the improved methods described herein remove systematic errors that may have previously existed and provide assurance that a target region can be accurately aligned with the actual isocentre of a treatment beam, and thus pinpointed for irradiation.

The repositioning of a patient for radiotherapy treatment, taking into account the different possible isocentre positions for different respective treatment beams as described herein, can involve moving the patient, and/or moving the patient positioning surface, and/or moving or altering another part of the radiotherapy device or radiotherapy system. Moreover, any such movement or alteration can be incorporated into, or added onto, pre-existing processes for patient positioning before/during radiotherapy treatment. As detailed above, the movement or alteration that is required according to the improved methods described herein may be actioned in isolation, or they may be added to other movements or alterations that are required for correct patient positioning. In either case, the movements or alterations required by the improved methods described herein can be made quite quickly and easily, thus not slowing down the patient set up time significantly, if at all, and not causing undue discomfort or upset to the patient.

The manner in which a patient and patient positioning surface (pps) can be moved is well known to the skilled reader and thus has not been described in detail herein. It is typical for a pps (or 'table' or 'couch') to be moveable up and down, left to right and forwards and backwards. It may also be rotatable about one or more of its axes (i.e. major/longitudinal axis and minor/lateral axis). A pps may be tiltable (i.e. pivotable), relative to the horizontal. The entire pps may be tiltable, or it may comprise one or more hinge-points, about which a section or sections may be tiltable.

Instead of or as well as moving the patient and/or pps, the improved methods described herein encompass moving one or more other parts of a radiotherapy device or radiotherapy system, in order to change a spatial relationship and thus achieve accurate alignment between a patient's anatomy and the 'real' isocentre of the treatment beam, with which the patient is to be treated. For example, it may be possible to shift the rotatable gantry, in a vertical and/or a horizontal direction, relative to the pps. For example, it may be possible to change the position of the treatment beam source, for example to change exactly where or how it attaches to the rotatable gantry. Other aspects may also or instead be moveable or changeable, dependent on the particulars of the individual radiotherapy system and on the movements or alterations required to achieve alignment.

The improved methods described herein also encompass calculating a patient (or device) movement/alteration that is required for alignment of a patient (or of an image of the patient) with the real isocentre of a treatment beam, without actually realising or actioning that movement or alteration. The calculated movement may instead be stored in a suitable memory, for subsequent use. For example, it may be added to other calculated movements, for the determination of a net movement.

The improved methods described herein may be implemented on a pre-existing radiotherapy device and/or on a current or future radiotherapy device.

The improved methods described herein may be embodied on a computer-readable medium, which may be a non-transitory computer-readable medium. The computer-readable medium may carry computer-readable instructions arranged for execution upon a processor so as to make the processor carry out any or all of the improved methods described herein. The processor may be comprised within a controller or a computer or may be embodied within a radiotherapy device or a radiotherapy system.

The term "computer-readable medium" as used herein refers to any medium that stores data and/or instructions for causing a processor to operate in a specific manner. Such a storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

Any terms relating to position such as 'vertical', 'horizontal', 'up', 'down', 'left', 'right', 'forwards', 'backwards', 'longitudinal', 'lateral', major', 'minor', and so on are used herein in an illustrative manner, and should not be regarded as limiting.

It is to be understood that the above description is intended to be illustrative, and not restrictive. Many other implementations will be apparent to those of skill in the art upon reading and understanding the above description. Although the present disclosure has been described with reference to specific example implementations, it will be recognised that the disclosure is not limited to the implementations described, but can be practiced with modification and alteration insofar as such modification(s) and alteration(s) remain within the scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The invention claimed is:

1. A method of positioning a patient for radiotherapy treatment using a radiotherapy device, the method comprising:
- determining an identity of a first treatment beam that is to be used to treat the patient;
- determining an offset between a reference location and an isocentre location for the determined first treatment beam that is to be used to treat the patient, wherein the reference location comprises a location of an isocentre of a second treatment beam that has an identity that is different to the identity of the first treatment beam that is to be used to treat the patient; and
- changing a spatial relationship between the patient and at least a part of the radiotherapy device, according to the determined offset.

2. The method of claim 1, wherein the radiotherapy device is configured to move between at least a first configuration and a second configuration, wherein each of the first configuration and the second configuration are associated with a respective treatment beam identity, and wherein determining the identity of the treatment beam to be used to treat the patient comprises determining whether the radiotherapy device is in, or will be in, the first configuration or the second configuration.

3. The method of claim 2, wherein the first configuration is a coplanar configuration, and the second configuration is a non-coplanar configuration.

4. The method of claim 1, wherein the radiotherapy device is configured to deliver different treatment beams from each of a plurality of angles with respect to a patient longitudinal axis, and wherein determining the identity of the treatment beam to be used to treat the patient comprises determining which angle of the plurality of angles the treatment beam will be delivered from.

5. The method of claim 1, wherein the identity of the treatment beam that is to be used to treat the patient comprises one or more characteristics of the treatment beam that is to be used to treat the patient, wherein the one or more characteristics comprises at least one of:

an angle at which the treatment beam is delivered;
an energy at which the treatment beam is delivered;
a beam profile;
a presence or an absence of a filter on the treatment beam; and
when a filter is present, a type of filter.

6. The method of claim 1, further comprising:

aligning an image of the patient to a focal point, wherein the focal point comprises the reference location;
determining an offset between a location of the focal point and a location of the isocentre of the treatment beam that is to be used to treat the patient; and
changing a spatial relationship between the patient and at least a part of the radiotherapy device, according to the determined offset of the location of the focal point and the location of the isocentre.

7. The method of claim 6, wherein the focal point has a location that coincides with a location of an isocentre of the second treatment beam, having a second identity, wherein the second treatment beam is not intended to be used to treat the patient; and wherein the method comprises:

determining an offset between the location of the isocentre of the second treatment beam and a location of an isocentre of the first treatment beam, having a first, different identity; and
changing a spatial relationship between the patient and at least a part of the radiotherapy device, according to the determined offset between the location of the isocentre of the first treatment beam and the location of the isocentre of the second treatment beam.

8. The method of claim 1, further comprising, before carrying out the steps of claim 1:

obtaining a location of a first isocentre, of the first treatment beam having a first identity;
obtaining a location of a second isocentre, of the second, different treatment beam having a second, different identity; and
determining a relative location between the first isocentre and the second isocentre.

9. The method of claim 8, wherein the location of the second isocentre comprises the reference location and the location of the first isocentre comprises the isocentre location for the determined treatment beam that is to be used to treat the patient, and wherein the offset is determined according to the relative location between the first isocentre and the second isocentre.

10. The method of claim 1, further comprising, before carrying out the steps of claim 1:

obtaining an image of the patient;
obtaining a location of a focal point of the image;
obtaining a location of a beam isocentre for each beam of a plurality of treatment beams, wherein each beam of the plurality of treatment beams have different respective identities; and
determining a relative location between each of the beam isocentre and the focal point of the image.

11. The method of claim 1, wherein the positioning of a patient for radiotherapy treatment using a radiotherapy device is carried out before radiotherapy treatment commences or during radiotherapy treatment.

12. The method of claim 1, wherein changing a spatial relationship between the patient and at least a part of the radiotherapy device, comprises:

adding the determined offset to a second, different, offset to produce a combined offset; and
changing the spatial relationship between the patient and at least a part of the radiotherapy device according to the combined offset.

13. The method of claim 8 comprising:

receiving an instruction to obtain an updated location of the second isocentre; and
obtaining an updated location of the second isocentre, in response to the instruction.

14. A method of determining a positioning for a patient for radiotherapy treatment using a radiotherapy device, the method comprising:

determining an identity of a first treatment beam that is to be used to treat the patient;
determining an offset between a reference location and an isocentre location for the determined first treatment beam that is to be used to treat the patient, wherein the reference location comprises a location of an isocentre of a second treatment beam that has an identity that is different to the identity of the first treatment beam that is to be used to treat the patient; and
determining a change in spatial relationship, between the patient and at least a part of the radiotherapy device, according to the determined offset.

15. A radiotherapy system comprising:

a radiotherapy device comprising a treatment apparatus for providing a radiotherapy treatment beam;
a patient positioning surface; and
a controller configured to:
determine an identity of a first treatment beam that is to be used to treat the patient;
determine an offset between a reference location and an isocentre location for the determined first treatment beam that is to be used to treat the patient, wherein the reference location comprises a location of an isocentre of a second treatment beam that has an identity that is different to the identity of the first treatment beam that is to be used to treat the patient; and
change a spatial relationship between the patient and at least a part of the radiotherapy device, according to the determined offset.

16. The radiotherapy system of claim 15, wherein the radiotherapy device is configured to deliver radiation in each of a coplanar configuration and at least one non-coplanar configuration.

17. The radiotherapy system of claim 15, further comprising:

a patient positioning apparatus comprising the patient positioning surface and configured, when a patient is positioned on the patient positioning surface, to change the spatial relationship between the patient and at least a part of the radiotherapy device.

18. The radiotherapy system of claim 15, further comprising:

a gantry adjustment apparatus configured, when a patient is positioned on the patient positioning surface, to change the spatial relationship between the patient and at least a part of the radiotherapy device.

19. A non-transitory computer readable storage medium comprising computer-executable instructions which, when executed by a processor of a computer, cause the computer to:

determine an identity of a first treatment beam that is to be used to treat a patient;

determine an offset between a reference location and an isocentre location for the determined first treatment beam that is to be used to treat the patient, wherein the reference location comprises a location of an isocentre of a second treatment beam that has an identity that is different to the identity of the first treatment beam that is to be used to treat the patient; and change a spatial relationship between the patient and at least a part of a radiotherapy device, according to the determined offset.

* * * * *